(12) United States Patent
Unger et al.

(10) Patent No.: US 7,415,146 B2
(45) Date of Patent: Aug. 19, 2008

(54) METHOD AND APPARATUS TO DETERMINE BONE MINERAL DENSITY UTILIZING A FLAT PANEL DETECTOR

(75) Inventors: Christopher D. Unger, Delafield, WI (US); Jianguo Zhao, Niskayuna, NY (US); Gopal Avinash, New Berlin, WI (US); Carson Thomas, Brookfield, WI (US); Jeffrey W. Eberhard, Albany, NY (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 463 days.

(21) Appl. No.: 10/063,338

(22) Filed: Apr. 12, 2002

(65) Prior Publication Data

US 2003/0194120 A1 Oct. 16, 2003

(51) Int. Cl.
*G06K 9/00* (2006.01)
*G01N 23/00* (2006.01)
*G01N 23/06* (2006.01)

(52) U.S. Cl. .......................... 382/132; 128/922; 378/5; 378/51

(58) Field of Classification Search ................. 382/128, 382/132
See application file for complete search history.

(56) References Cited

U.S. PATENT DOCUMENTS

| 4,626,688 | A | * | 12/1986 | Barnes | 250/361 R |
| 5,638,458 | A | * | 6/1997 | Giger et al. | 382/132 |
| 6,173,034 | B1 | * | 1/2001 | Chao | 378/37 |
| 6,303,573 | B1 | * | 10/2001 | Ruoslahti et al. | 514/12 |
| 6,690,761 | B2 | * | 2/2004 | Lang et al. | 378/56 |

(Continued)

OTHER PUBLICATIONS

Laskey et al, "Dual-Energy X-Ray Absorptiometry and Body Composition", Nutrition, vol. 12, No. 1, 1996, pp. 45-51.*

(Continued)

*Primary Examiner*—Charles Kim
(74) *Attorney, Agent, or Firm*—McAndrews, Held & Malloy, Ltd.; Peter J. Vogel; Michael A. Dellapenna (57) ABSTRACT

A method and apparatus for using a flat panel detector to determine bone mineral density are provided. The apparatus includes a dual energy X-ray emitter, a flat panel detector for receiving X-rays sent from the X-ray emitter, and may optionally include an image corrector, adapted to emit corrected image information. The apparatus also includes a basis material decomposer that includes a calibration database, the decomposer being adapted to create a bone image and a soft tissue image. The apparatus further includes a bone mineral density calculator that is adapted to compute bone mineral density from the first image, and a display for displaying at least the computed bone mineral density. A method for using a flat panel detector to detect multiple disease states is also provided. The method includes emitting X-rays from a dual energy X-ray source through an area of a patient's body sought to be imaged and receiving X-rays with a flat panel detector. The method also includes generating multiple images, using dual energy X-ray absorptiometry, to detect for a first disease state and a second disease state and analyzing the images for the first and second disease states. The first disease state includes lung cancer, breast cancer, pneumonia, chronic obstructive pulmonary disease, tuberculosis, bone fracture or an abnormally sized or shaped organ and the second disease state comprises osteoporosis.

4 Claims, 7 Drawing Sheets

U.S. PATENT DOCUMENTS 6,816,564 B2 * 11/2004 Charles et al. .............. 378/5

OTHER PUBLICATIONS

Sievanen et al, "Estimation of Various Mechanical Characteristics of Human Bones during Dual Energy X-ray Absorptiometry: Methodology and Precision", Bone, vol. 18, issue 1, supplement 1, Jan. 1996, pp. 17-27.*

Smith et al. "Dual X-ray absorptiometry detects disease- and treatment-related alterations of bone density in prostate cancer patients", Clinical and Experimental Metastasis vol. 18, No. 5 / Sep. 2000.*

* cited by examiner

METHOD AND APPARATUS TO DETERMINE BONE MINERAL DENSITY UTILIZING A FLAT PANEL DETECTOR

BACKGROUND OF INVENTION

Certain embodiments of the present invention relate to the detection of osteoporosis and more particularly relates to the detection of bone mineral density using a flat panel detector.

Osteoporosis is a disease of the skeleton in which the amount of calcium present in the bones slowly decreases to the point where the bones become brittle and prone to fracture. In other words, the bone loses density. Osteoporosis is diagnosed when bone density has decreased to the point where fractures occur even under mild stress, also referred to as the fracture threshold.

In the United States alone, ten million people have osteoporosis and eighteen million more have low bone mass (80% of whom are women), a condition which indicates an increased risk of developing osteoporosis. Osteoporosis is responsible for one-and-one-half million fractures annually. As a result, statistics indicate that one of every two women over age fifty will have an osteoporosis-related fracture in their lifetime. As a reference, a woman's risk of an osteoporosis-related fracture is equal to her combined risk of acquiring breast, uterine and ovarian cancer. The most common sites of fractures are the hip, spine, wrist and ribs. Perhaps the most devastating of these fractures is the hip fracture. On average, 24% of hip fractures in patients 50 and over lead to death within one year. Osteoporotic fractures such as these cost an estimated $18 billion annually.

Unfortunately, bone density loss occurs without symptoms. Bone mineral density (BMD) measurements can be used to detect osteoporosis before fracture, determine the probability of a future fracture, determine the rate of bone loss, and monitor the efficacy of treatment. Additionally, effective treatments currently exist, thus highlighting the desirability for early detection of the disease. Nonetheless, due to the lack of symptoms, osteoporosis is underdiagnosed and frequently goes undetected.

Due to the frequency of osteoporotic fractures, the National Osteoporosis Foundation (NOF) currently recommends broad categories of women to receive bone mineral density testing: all women ages 65 and older, postmenopausal women having any of the risk factors for osteoporotic fracture (low body weight, history of fracture, Asian or Caucasian, cigarette smoking, estrogen deficiency, early menopause, low calcium intake, alcoholism, recurrent falls, and inadequate physical activity), and all postmenopausal women who have already had a fracture. Additionally, many women with these same risk factors are recommended to have mammography tests. It may also be desirable to test women with these same risk factors for lung cancer, pneumonia, or a bone fracture.

There are two basic methods to measure the density of bone. These methods involve passing either X-rays or ultrasound waves through the bone being assessed, and measuring the effect that the bone has on these rays or waves. Within the field of X-rays, the measurement may utilize the principals of either radiogrammetry (i.e., standard X-ray techniques) or absorptiometry. In this context, radiogrammetry (or radiography) involves the use of registration on film of the differential absorption of X-ray beams passing through a specimen. Absorptiometry refers to a chemical analysis of gases, liquids or solids to measure densities, porosities as well as coating, plating and insulation thickness. In the context of osteoporosis, absorptiometry is use to measure bone densities. There are two types of absorptiometry, single energy X-ray absorptiometry ("SXA") and dual energy X-ray absorptiometry ("DXA"). Single energy X-ray absorptiometry involves the use of X-rays at a single wavelength to measure bone mineral content (in the detection of osteoporosis). Dual energy X-ray absorptiometry involves the use of X-rays at two wavelengths to measure bone mineral content (in the detection of osteoporosis). DXA is used when SXA is not feasible, i.e., in areas with variable soft tissue and composition such as the spine or hip.

Two types of BMD tests used in diagnosing osteoporosis that utilize X-rays are peripheral BMD on the wrist or heel (radiogrammetry using a pencil beam or a fan beam), and dual energy X-ray absorptiometry on the hip, spine or femur. For example, osteoporosis tests and lung cancer tests are currently performed in separate units and/or stations (in separate rooms or areas): the osteoporosis test using a pencil beam or fan beam on the heel or wrist, and the lung cancer test using a standard radiography unit. While the scanning time for X-rays is generally short (on the order of less than one second), the setup time for each of these tests can take ten minutes or more.

Due to the overlap in symptoms, ages and gender in people who have osteoporosis and/or other disease states (e.g., breast cancer, lung cancer and pneumonia, chronic obstructive pulmonary disease, tuberculosis, bone fracture or an abnormally sized or shaped organ), there is a particular need for a dual-purpose screening method capable of detecting both osteoporosis (or BMD) and at least one other disease state.

SUMMARY OF INVENTION

Certain embodiments relate to an apparatus for using a flat panel detector to determine bone mineral density. The apparatus includes a dual energy X-ray emitter, a flat panel detector for receiving X-rays sent from the X-ray emitter, and may optionally include an image corrector adapted to provide corrected image information. The apparatus also includes a basis material decomposer comprising a calibration database. The decomposer is adapted to create first and second images, the first image comprising a bone image and the second image comprising a soft tissue image. The apparatus further includes a bone mineral density calculator adapted to compute bone mineral density from the first image, and a display for displaying at least the computed bone mineral density.

Certain embodiments relate to a method for using a flat panel detector to detect multiple disease states. The method includes emitting X-rays from a dual energy X-ray source through an area of a patient's body sought to be imaged and receiving X-rays with a flat panel detector. The method also includes generating multiple images, using dual energy X-ray absorptiometry, to detect for a first disease state and a second disease state and analyzing the images for the first and second disease states. The first disease state includes lung cancer, breast cancer, pneumonia, chronic obstructive pulmonary disease, tuberculosis, chronic obstructive pulmonary disease, bone fracture or an abnormally sized or shaped organ and the second disease state comprises osteoporosis. The analyzing step may optionally include determining the aerial density ($g/cm^2$) or volume density ($g/cm^3$) of a bone sought to be imaged.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
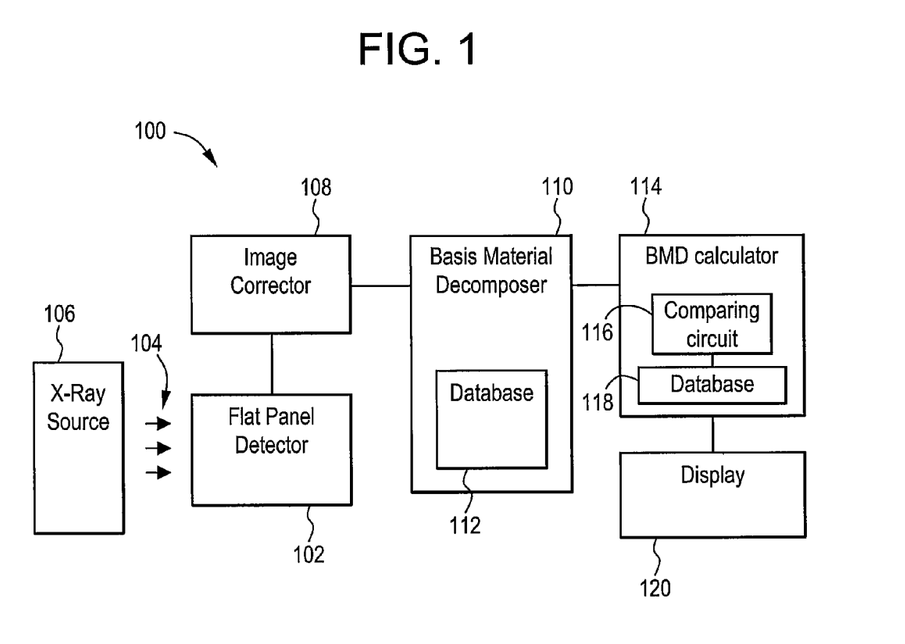
FIG. 1 illustrates an apparatus using a flat panel detector to determine bone mineral density according to one embodiment of the present invention.
Figure 2:
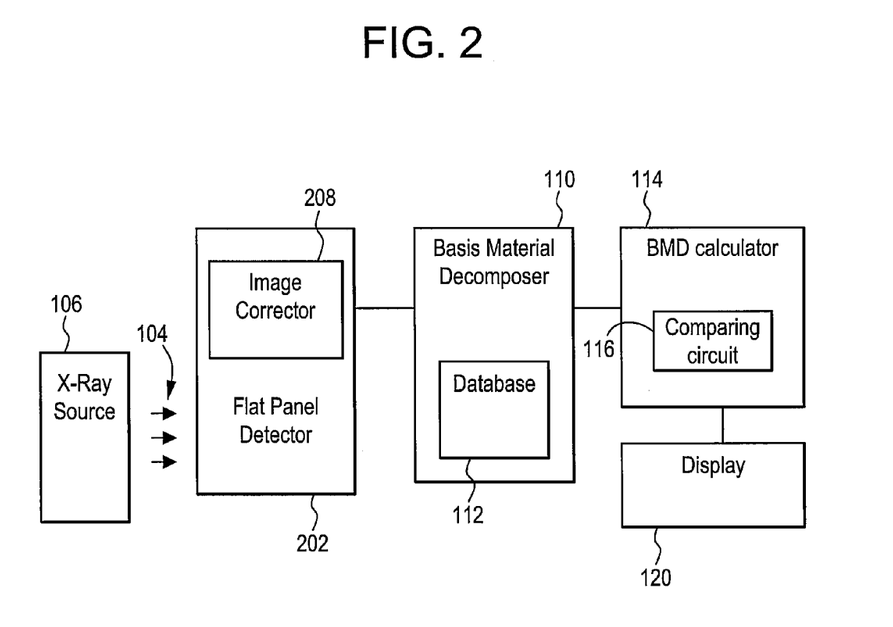
FIG. 2 illustrates an apparatus using a flat panel detector to determine bone mineral density according to another embodiment of the present invention.

Turning to FIGS. 1 and 2, an apparatus 100 utilizing a flat panel detector (FPD) 102 to measure bone mineral density and detect osteoporosis is shown. In order to use the FPD 102 in this manner, dual energy X-rays 104 (i.e., both a high energy X-ray and a low energy X-ray following one another in time) are emitted in succession from an X-ray source 106 and passed through the portion of the body sought to be imaged. High energy X-rays 104 and low energy X-rays 104 are received by the FPD 102 at separate times and two images are created, a high-energy image and a low-energy image, respectively. The images may be displayed or may simply be stored as data. The image corrector 108 corrects the images for artifacts, scatter, etc. (using, for example, calibration values) to compensate for imperfections in the X-ray source 106 or FPD 102.

In further detail, the dual energy flat panel detector (FPD) 102 takes two successive X-ray images of the chest at different energy levels. The dual energy X-rays include a high energy (e.g., 110-150 kVp) and a low energy (e.g., 60-80 kVp) X-ray. The successive X-ray images are generally taken less than one second apart, for example, about 200 milliseconds apart.

Once the images are corrected, a basis material decomposition is performed using the basis material decomposer 110. The basis material decomposer 110 estimates and separates the X-ray absorption caused by the soft tissue and the X-ray absorption caused by the bone (i.e., the hard tissue). The basis material decomposition is performed using the thicknesses of the bone and soft tissue (which are relatively easy to compute), and a table including calibration values for X-ray decomposition in various thicknesses of materials that are similar in content to bone and soft tissue.

Aluminum and lucite, respectively, are generally similar enough in content to use to predict how the X-ray 104 should be absorbed by the bone and soft tissue. Through the use of the calibration table with the basis material decomposer 110, the amount of absorption caused by the bone and soft tissue, respectively, is estimated. From the separation of the bone and soft tissue data, bone and soft tissue images are generated. The images may be displayed on a monitor for viewing.

Referring to FIGS. 1, 2, 6 and 7, the bone image is used to detect BMD or osteoporosis as follows. Beginning with the method of FIG. 6, a basis mineral decomposition is performed at step 602 using a basis material decomposer 110. The basis material decomposer 110 may include a database 112 of estimates of X-ray absorption from materials approximating bone and soft tissue, for various thicknesses, including the estimated thickness of bone and/or soft tissue depicted in the image. As described above, two materials which may be useful for estimating the X-ray absorption are lucite and aluminum, for soft tissue and bone, respectively. Second, a bone mineral density is calculated at step 604, for example using a bone mineral density calculator 114. The calculated bone mineral density is then compared at step 606 to at least one predetermined bone mineral density using the comparing circuit 116. The BMD comparison at step 606 may compare the patient's BMD to the average, mean, etc. of BMD in people who should have similar bone mineral densities (e.g., people of the same race, gender, age, etc.). The BMD comparison at step 606 may additionally or alternatively be performed for previous BMD calculations for the same patient (e.g., to see how the disease is progressing, whether it has been arrested, and/or whether medication is proving successful). To accomplish the comparison at step 606, the bone mineral density calculator 114 and/or comparing circuit 116 may include a database 118 of bone mineral densities for the same patient or a table of bone mineral densities for other people. Once the comparison at step 606 is complete, the calculated bone mineral density, other predetermined bone mineral densities and/or the images may be presented on a display 120 for a physician's review 710.

Figure 6:
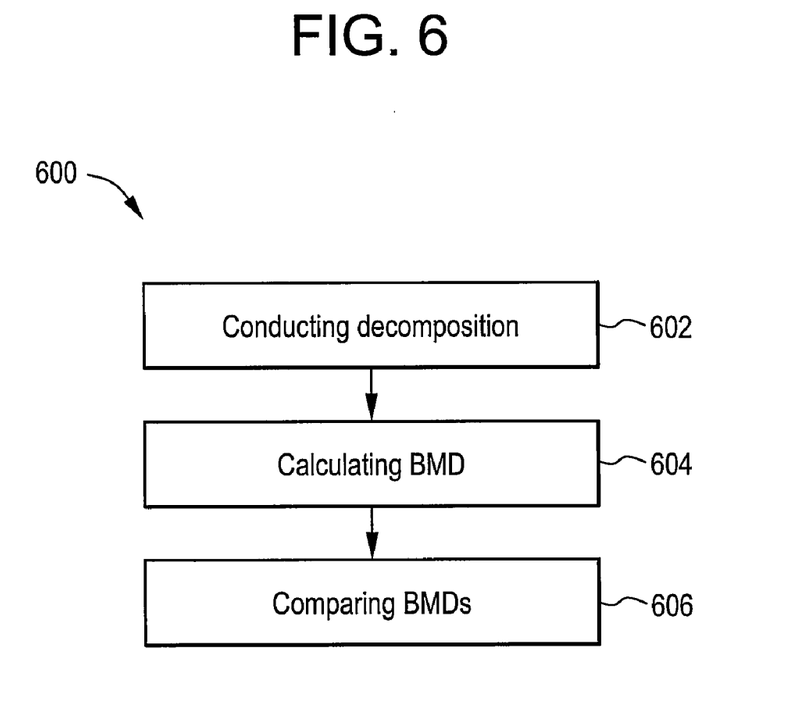
FIG. 6 illustrates a method of determining bone mineral density according to still another embodiment of the present invention.

Focusing in particular on the bone image, the bone mineral density calculator 114 calculates BMD "score," e.g., a relative intensity is determined from comparing the intensity of the X-rays absorbed passing through the bone to a baseline (i.e., where the X-rays 104 did not pass through bone). The relative intensity may be determined by comparing the bone intensity to the non-bone intensity in either the bone image or the soft tissue image (or a combination of both). The relative density is referred to as the aerial density of the bone and/or the BMD score. Once the BMD score is calculated at step 604, it is compared to either a population table or prior data for the patient using the comparing circuit 116. The population table is a table of bone density score information that may be based on many factors: age, gender, ethnicity, medications a patient is taking, etc. Prior data for the particular patient may include, for example, prior BMD scores or earlier radiographic images of the patient. In comparing at step 606 the BMD score to prior data for the patient, it may be determined whether a patient's osteoporosis is progressing or whether a patient's medications are treating the disease effectively. Thus, the physician reviewing the bone image and associated BMD information is able to analyze whether a patient has osteoporosis or whether the patient's medication is effectively treating the disease.

Referring generally to FIG. 1, the X-ray source 106, FPD 102, image corrector 108, 208, basis material decomposer 110, BMD calculator and display 120 may be implemented using combinatorial logic, an ASIC, through software implemented by a CPU, a DSP chip, or the like. Additionally, the foregoing hardware elements may be part of hardware that is used to perform other operational functions. The databases 112, 118, comparing circuit 116, intensities BMD scores and tables may be stored in registers, RAM, ROM, or the like, and may be generated through software, through a data structure located in a memory device such as RAM or ROM, and so forth.

The apparatus 100 may also be included in one of the following: a radiography unit (or RAD unit), a mammography unit, a cardiography unit, or a vascular imaging system. In this way, the apparatus 100 can be utilized in a way that enables a patient to be diagnosed for osteoporosis as well as another disease state without having to sit through two full exams.

According to the method illustrated in part in FIGS. 3-7, an X-ray source 106 emits at step 302 a high energy X-ray and a low energy X-ray through a portion of the body sought to be imaged. After passing through the portion of the body sought to be imaged, the FPD receives at step 304 the high and low energy X-rays (e.g., the unabsorbed portions thereof).

Figure 3:
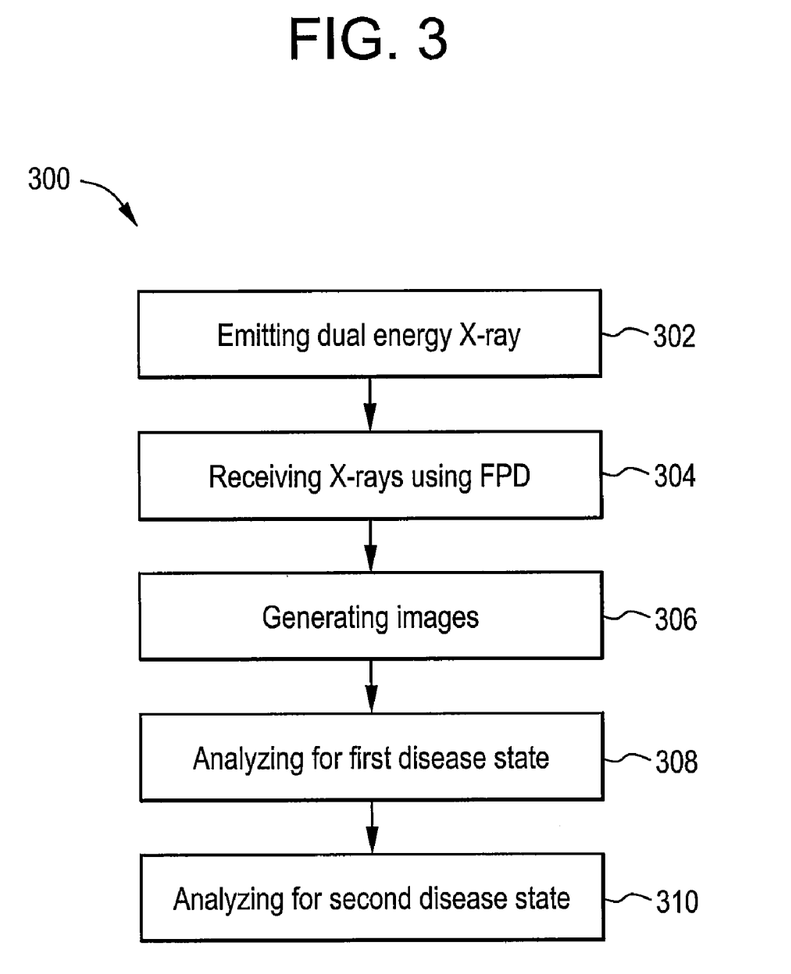
FIG. 3 illustrates a method of using a flat panel detector to detect multiple disease states according to one embodiment of the present invention.

Once received, the unabsorbed high and low energy X-rays are used in conjunction with dual energy imaging software or a dual energy imaging algorithm to generate multiple images at step 306. In one embodiment, when used to image the chest, the dual energy X-ray 104 is used to generate a standard posterior-anterior (PA) X-ray image, a PA image of the chest with the bones removed ("soft tissue image"), and an image of the skeletal system of the chest ("bone image").

Once these images are created, the physician analyzes at steps 308, 310 the images to detect multiple disease states. For example, the soft tissue image may be used to detect lung cancer or pneumonia and the bone image may be used to detect BMD or osteoporosis. The analysis of the bone image may include determining the aerial density ($g/cm^2$) or volume density ($g/cm^3$) of the bone of interest. This analysis may involve, for example, the use of image processing and segmentation algorithms.

As a result, with the use of the FPD 102 alone and only one exam, a physician can check a patient, for example, for both lung cancer and osteoporosis. A physician can also check for breast cancer and osteoporosis, which is desirable because their risk factors overlap significantly.

Figure 7:
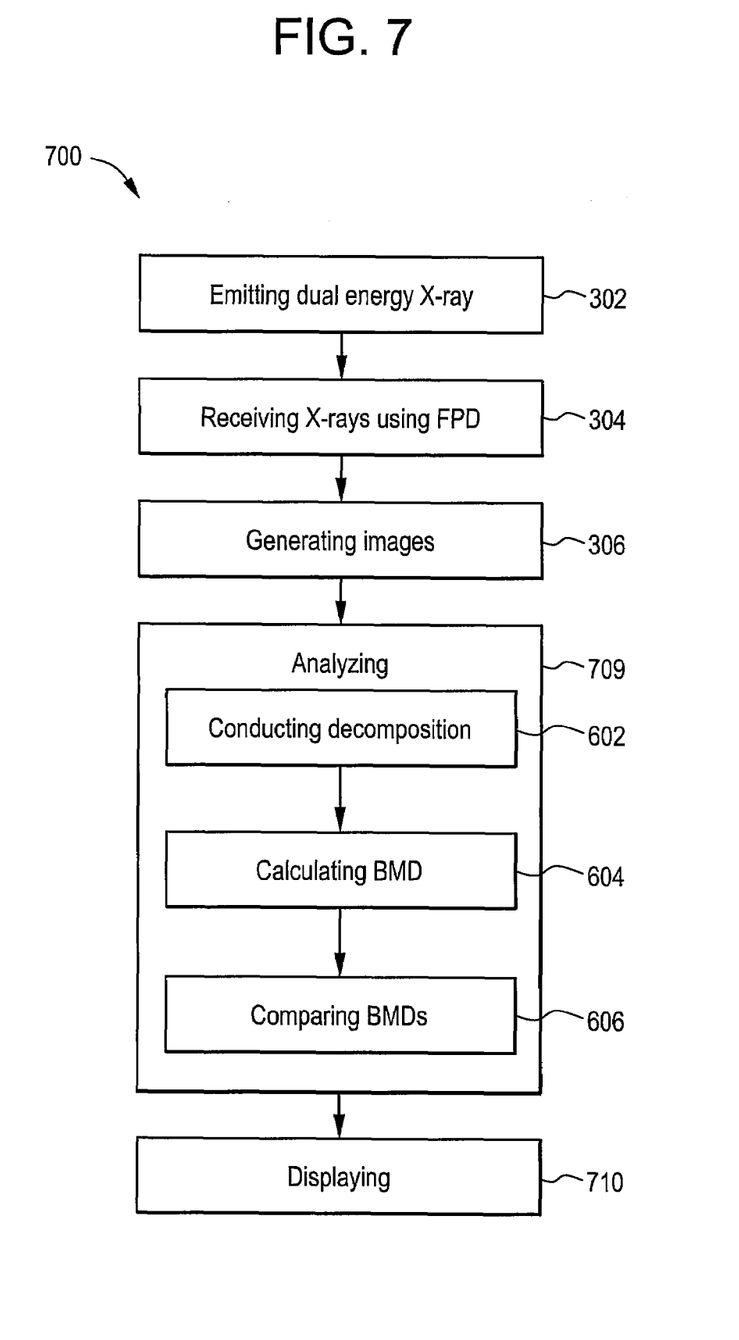
FIG. 7 illustrates a method of using a flat panel detector to determine bone mineral density according to one embodiment of the present invention.

Referring FIGS. 3, 6 and 7, a physician may analyze 308 the standard radiograph or a soft tissue image for at least the following: lung cancer, breast cancer, pneumonia, chronic obstructive pulmonary disease, tuberculosis, bone fracture or an abnormally sized or shaped organ. Utilizing the skeletal system image and the data displayed as a result of the basis material decomposition at step 602, BMD calculation at step 604 and BMD comparison at step 606, the physician may analyze at step 310 the image (and/or the displayed data associated with the image) for the detection of osteoporosis.

Figure 4:
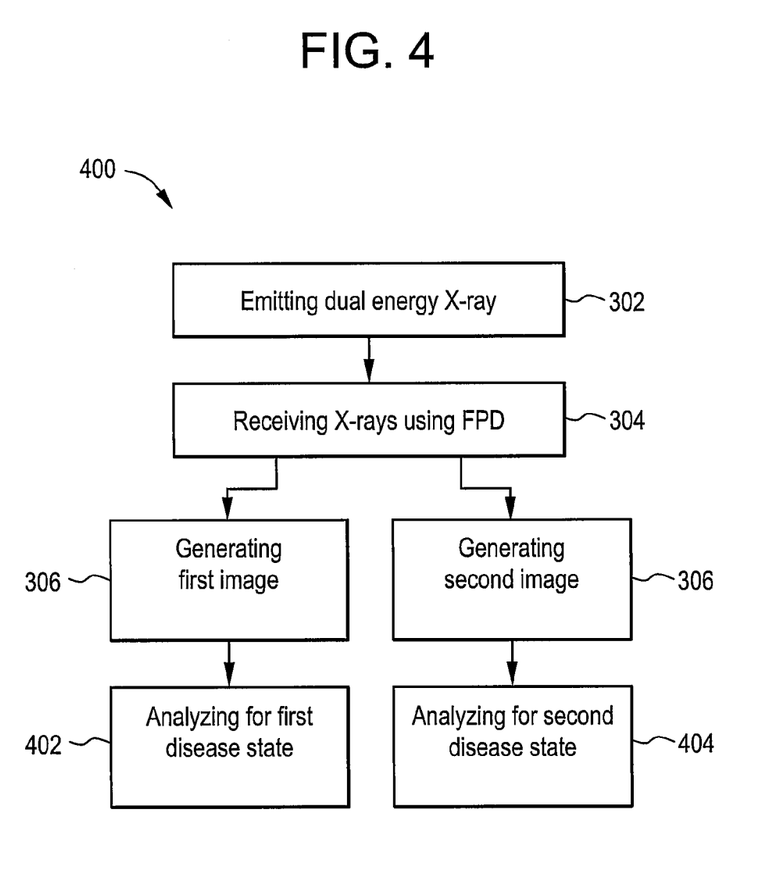
FIG. 4 illustrates a method of using a flat panel detector to detect multiple disease states according to another embodiment of the present invention.
Figure 5:
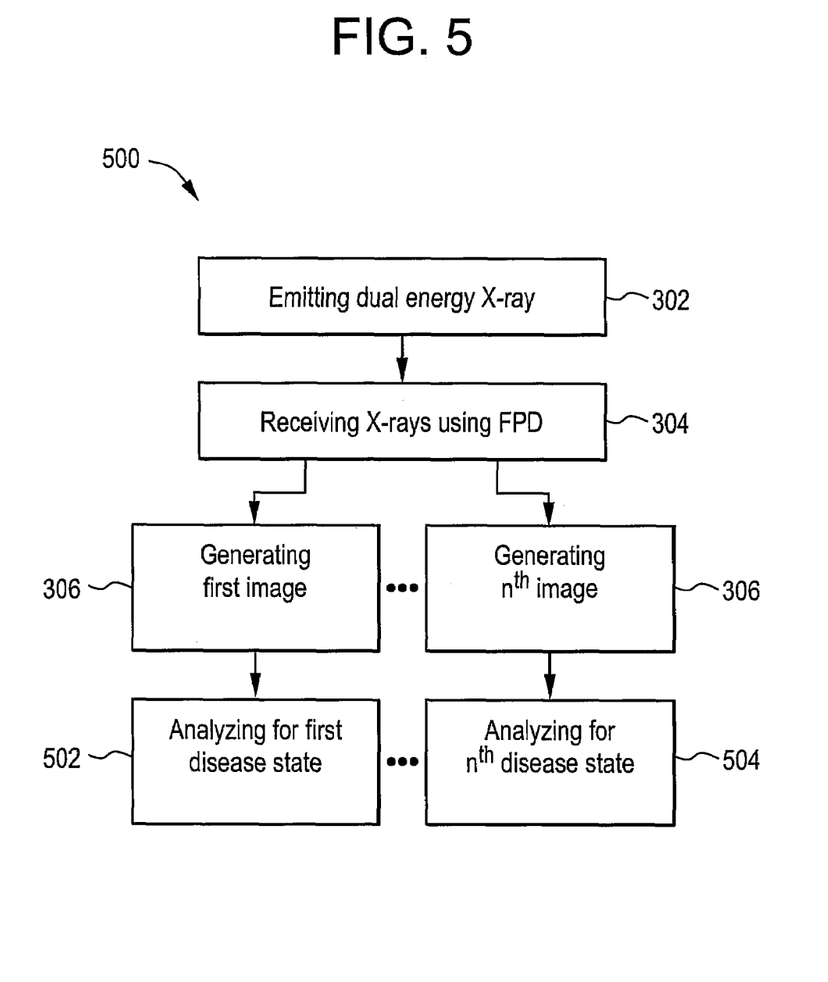
FIG. 5 illustrates a method of using a flat panel detector to detect multiple disease states according to yet another embodiment of the present invention.

As illustrated in FIG. 3, the analysis for the first and second disease states at steps 308, 310 may be performed in series by one physician. As illustrated in FIG. 4, however, the analysis may be performed in parallel by multiple physicians or at separate times at steps 402, 404. For example, a physician administering the flat panel scan is knowledgeable in reading mammograms, but may not skilled in diagnosing osteoporosis or understanding the bone mineral density information. He or she may have the image reviewed later by a colleague at the same location who is skilled in diagnosing osteoporosis, or even send a bone image to an osteoporosis specialist in another location (either by teleradiography or otherwise). As illustrated in FIG. 5, n images may be generated by the FPD and analyzed for n disease states at steps 502, 504. For example, one physician who is competent to read a standard radiograph for a broken bone, may desire others to diagnose the patient for breast cancer and osteoporosis. He or she can send the soft tissue image to a breast cancer specialist and a bone image to an osteoporosis expert (either by teleradiography or otherwise). Thus, three separate physicians can review the images to diagnose three different disease states (in this case, bone fracture, breast cancer and osteoporosis).

Of course, the availability of multiple images may be useful in diagnosing each individual disease state. For example, in lung cancer screening, a soft tissue image may show nodules and a bone image may show whether or not such nodules are calcified. Both would be useful in diagnosing bone cancer. The method illustrated in FIG. 3 demonstrates that the parallel analysis permitted in FIGS. 4 and 5 is not required.

In short through the use of only one dual energy x-ray, the physicians may determine bone mineral density, analyze for osteoporosis and/or analyze for multiple disease states, osteoporosis and one or more of several others. With the ability to perform tests for multiple disease states with only one dual energy X-ray 104 (or multiple dual energy X-rays using the same unit), the time required to test for multiple disease states may be significantly decreased. The X-ray or radiation exposure to test for multiple disease states may also be reduced.

Detection for multiple disease states may help prolong lives and is economically sensible. Due to the increased health care needs and increased likelihood of death associated with bone fractures among the elderly, early detection of osteoporosis is desirable. Because osteoporosis is treatable, early detection may extend the healthy lives of those with the disease.

While particular embodiments of the invention have been shown, it will be understood, of course, that the invention is not limited thereto since modifications may be made by those skilled in the art, particularly in light of the foregoing teachings. It is, therefore, contemplated that the appended claims will cover any such modifications as incorporate those features that constitute the essential features of these improvements within the true spirit and the scope of the invention.

The invention claimed is:

1. A method for using a flat panel detector to diagnose a patient for two or more disease states as a result of a single exam, comprising:

emitting X-rays from a dual energy X-ray absorptiometry source through at least a first portion of a patient's body sought to be imaged; receiving X-rays through the use of a flat panel detector; generating n images using a single emission from the dual energy X-ray absorptiometry source, based on signals read out of the flat panel detector, to diagnose n disease states as a result of a single exam, wherein n is an integer greater than 2; and analyzing at least the n images for n disease states, wherein at least one image is analyzed for osteopenia, said osteopenia analyzing step comprising: calculating a bone mineral density based on signals read out of the flat panel detector;

comparing said bone mineral density to at least one predetermined bone mineral density using a comparing circuit; and displaying a result of said comparison on a display.

2. The method of claim 1 wherein said at least one predetermined bone mineral density comprises at least one bone mineral density previously calculated for the patient.

3. The method of claim 1 wherein said at least one predetermined bone mineral density is stored in a database that comprises bone mineral densities.

4. The method of claim 1 wherein the emitting step comprises emitting X-rays from the dual energy X-ray absorptiometry source through at least said first portion and a second portion of a patient's body sought to be imaged.

* * * * *